US008141795B2

(12) United States Patent
Dvorsky et al.

(10) Patent No.: US 8,141,795 B2
(45) Date of Patent: Mar. 27, 2012

(54) AEROSOL DISPENSING DEVICE AND METHOD

(75) Inventors: James E. Dvorsky, Hilliard, OH (US); Beverly A. Piatt, Columbus, OH (US)

(73) Assignee: Battelle Memorial Institute, Columbus, OH (US)

(*) Notice: Subject to any disclaimer, the term of this patent is extended or adjusted under 35 U.S.C. 154(b) by 0 days.

(21) Appl. No.: 12/859,867

(22) Filed: Aug. 20, 2010

(65) Prior Publication Data
US 2010/0314460 A1 Dec. 16, 2010

Related U.S. Application Data

(63) Continuation of application No. 11/351,832, filed on Feb. 10, 2006, now Pat. No. 7,798,420.

(60) Provisional application No. 60/652,059, filed on Feb. 11, 2005, provisional application No. 60/652,060, filed on Feb. 11, 2005, provisional application No. 60/652,064, filed on Feb. 11, 2005, provisional application No. 60/652,057, filed on Feb. 11, 2005, provisional application No. 60/652,067, filed on Feb. 11, 2005.

(51) Int. Cl.
*B05B 5/025* (2006.01)
*B05B 5/00* (2006.01)
*B05B 9/00* (2006.01)

(52) U.S. Cl. ......................... 239/326; 239/145; 239/690

(58) Field of Classification Search ................ 239/3, 11, 239/34, 44, 67–70, 102.1, 145, 302, 326, 239/690, 696, 697, 706, 707; 128/200.14, 128/203.15; 204/450, 600
See application file for complete search history.

(56) References Cited

U.S. PATENT DOCUMENTS

| | | | |
|---|---|---|---|
| 4,356,528 | A | 10/1982 | Coffee |
| 4,580,721 | A | 4/1986 | Coffee et al. |
| 4,776,515 | A | 10/1988 | Michalchik |
| 4,962,885 | A | 10/1990 | Coffee |
| 5,115,131 | A | 5/1992 | Jorgenson et al. |
| 5,121,884 | A | 6/1992 | Noakes |
| 5,184,778 | A | 2/1993 | Noakes |
| 5,196,171 | A | 3/1993 | Peltier |
| 5,322,684 | A | 6/1994 | Barnett et al. |
| 5,337,963 | A | 8/1994 | Noakes |
| 5,382,410 | A | 1/1995 | Peltier |
| 5,503,335 | A | 4/1996 | Noakes et al. |
| 5,655,517 | A | 8/1997 | Coffee |
| 5,810,265 | A | 9/1998 | Cornelius et al. |
| 5,927,618 | A | 7/1999 | Jefferies et al. |
| 5,975,426 | A | 11/1999 | Myers |
| 6,302,331 | B1 | 10/2001 | Dvorsky et al. |

(Continued)

FOREIGN PATENT DOCUMENTS

| | | | |
|---|---|---|---|
| EP | 0120633 | B1 | 12/1988 |

(Continued)

*Primary Examiner* — Darren W Gorman

(74) *Attorney, Agent, or Firm* — Stevens & Showalter LLP

(57) ABSTRACT

A method for delivering an aerosol, especially an aromatic aerosol, comprising the steps of contacting a capillary wick, comprising an EHD comminution site, with a liquid source, whereby at least a portion of the liquid transports to the EHD comminution site; applying a voltage to the liquid within the capillary wick at a location spaced apart from the liquid source and proximate the EHD comminution site; and applying a ground reference at a location external to the EHD comminution site, wherein at least a portion of the liquid EHD comminutes to form a spray having a generally-consistent flowrate and a device therefor.

5 Claims, 5 Drawing Sheets

U.S. PATENT DOCUMENTS

| | | |
|---|---|---|
| 6,311,903 B1 | 11/2001 | Gaw et al. |
| 6,318,640 B1 | 11/2001 | Coffee |
| 6,397,838 B1 | 6/2002 | Zimlich, Jr. et al. |
| 6,454,193 B1 | 9/2002 | Busick et al. |
| 6,457,470 B1 | 10/2002 | Coffee |
| 6,682,004 B2 | 1/2004 | Kadlubowski et al. |
| 6,684,897 B2 | 2/2004 | Sundararajan |
| 6,729,552 B1 | 5/2004 | McEwen et al. |
| 6,753,521 B1 | 6/2004 | Park et al. |
| 6,789,741 B2 | 9/2004 | Varanasi et al. |
| 6,790,408 B2 | 9/2004 | Whitby et al. |
| 6,814,315 B2 | 11/2004 | Gould et al. |
| 6,832,794 B2 | 12/2004 | He et al. |
| 7,503,512 B2 | 3/2009 | Nakada et al. |
| 2002/0022040 A1 | 2/2002 | Robinson et al. |
| 2003/0173219 A1 | 9/2003 | Davies et al. |

FOREIGN PATENT DOCUMENTS

| | | | |
|---|---|---|---|
| EP | 0607182 B1 | 5/2001 | |
| WO | 0160526 A1 | 8/2001 | |
| WO | 0209889 A1 | 2/2002 | |
| WO | 02055209 A2 | 7/2002 | |
| WO | 02055210 A1 | 7/2002 | |
| WO | 02055211 A1 | 7/2002 | |
| WO | 02055212 A1 | 7/2002 | |
| WO | 03000431 A1 | 1/2003 | |
| WO | 03072263 A1 | 9/2003 | |
| WO | 03086488 A1 | 10/2003 | |
| WO | 2004038752 A2 | 5/2004 | |
| WO | 2004054627 A1 | 7/2004 | |
| WO | 2004110641 A1 | 12/2004 | |

AEROSOL DISPENSING DEVICE AND METHOD

CROSS-REFERENCE TO RELATED APPLICATION(S)

This application is a continuation application of U.S. patent application Ser. No. 11/351,832, filed Feb. 10, 2006, entitled "Aerosol Dispensing Device And Method," which claims priority to the following U.S. Provisionals: "High Voltage Apparatus for Aerosol Delivery", 60/652,059; "Apparatus for Aerosol Delivery Using Capillary Pumping from a Reservoir", 60/652,060; "Apparatus for Aerosol Delivery Using Capillary Pumping", 60/652,064; "Capillary Tip Geometries", 60/652,057; and "Capillary Wick Aerosol Candle", 60/652,067, the contents of each of which are fully incorporated herein.

STATEMENT REGARDING FEDERALLY-SPONSORED RESEARCH OR DEVELOPMENT

Not applicable.

INCORPORATION-BY-REFERENCE OF MATERIAL SUBMITTED ON A CD

Not applicable.

BACKGROUND OF THE INVENTION

1. Field of the Invention

This invention relates to a device and method for dispensing aerosol sprays in a manner which promotes rapid and consistent vaporization. In particular, the invention relates to dispensing aromas.

2. Background

There are various known techniques for dispensing or dispersing aromas or olfactory stimulants. For example, aromatic oils are often dispersed by application of heat to an evaporation surface. The heat may, however, detrimentally affect the aroma being dispensed. As well, where the aroma dispensing device comprises an aromatic candle, the vapors carrying the aroma are often denatured or oxidized in the candle flame, reducing the intrinsic or "natural" quality of the fragrance. Other aroma dispensing devices rely on the use of propellants or aerosols to enable the dispersion. However, such propellants and aerosols may also detrimentally affect the aroma being dispersed.

In the conventional aroma delivery devices described above, it is difficult to consistently and precisely control delivery of the sprayed material. For example, in the case of an aromatic candle or other aroma delivery device that operates by using heat causing evaporation, some degree of evaporation will continue after the candle has been blown out or the device has been switched off. In addition, such devices generate an aroma a single aroma, continuously as long as the device is activated. This causes saturation of the olfactory senses and the perceived fragrance declines. Also, aerosol cans and pump sprays may produce large droplets which do not vaporize well and tend to rapidly fall under gravity and settle, also resulting in a continuous or lingering aroma which may degrade with time. Other devices, such as solid evaporative devices, experience a decay in aroma delivery rate over time.

U.S. Pat. No. 5,196,171 to Peltier describes the generation of vapors and/or aerosols by applying a DC voltage to a wick-like, porous emitter. In this case, the wick comprises a porous "capillament assembly" in which is disposed a central conductive electrode. In operation, the liquid provides a means of conducting the charge from the center of the wick to the outer surface where vaporization takes place due to corona discharge. The greatest concentration of vapors is created at the corners and edges (points or sharp radius edges) where the corona discharge forms.

Aerosols may also be created by the application of electrohydrodynamic ("EHD") forces to a liquid. In doing so, the liquid forms a so-called Taylor cone at the EHD comminution site, becomes charged, and forms a jet or ligament which separates, or comminutes, into an aerosol. In utilizing EHD, it is desirable to keep voltages low to avoid corona discharge which is detrimental to the formation of aerosols. U.S. Pat. No. 5,337,963 to Noakes describes a spraying device which comprises a vertically-disposed capillary tube with one end immersed in a fragrance-producing oil. When an electrical potential is applied to the bulk liquid, generally near the submerged end of the capillary, the liquid is sprayed from the top end as a plurality of ligaments which break up into droplets. The applied electrical potential is reported to be in the range of 10-25 kV and must be high enough to cause EHD comminution at the top of the capillary. Liquid is fed by capillary action from a reservoir to the top end of the capillary for aerosolization. U.S. Pat. No. 5,503,335 to Noakes describes a similar spraying device, but which comprises a wick in place of the aforementioned capillary tube. The wick is fabricated from material having an open-celled structure. In this case as well, the high voltage is applied to the bulk liquid, generally near the submerged end of the wick. U.S. Pat. No. 5,810,265 to Cornelius et al. describes yet another similar spraying device, but which capillary structure comprises a hollow capillary tube having a convoluted inner surface to enhance capillary action. Similarly, the high voltage is applied to the bulk liquid, also generally near the submerged end of the capillary tube. Finally, U.S. Pat. No. 5,655,517 to Coffee describes a device for dispensing a comminuted liquid comprising a comminution site provided by fibers formed into a bundle projecting from an end surface or edge.

In the delivery devices described above, it is difficult to consistently and precisely control delivery of the spray. While EHD spraying offers many advantages, including the ability to produce consistent sprays of aerosol particles having a narrowly-tailored size distribution, significant inconsistencies were observed in the delivery rate of the liquid to the surrounding air.

It is, therefore, an object of the present invention to provide an aerosol delivery device that avoids or at least reduces adverse effects on an aroma resulting from the manner in which the aroma is delivered. It is another object of the present invention to provide an aerosol delivery device that enables improved control of delivery rate of the aerosol. It is yet another object of the invention to provide an aerosol delivery device that offers consistent aerosol delivery over the reservoir volume. It is a further object of the present invention to provide a method that offers the advantages of reduced adverse effects on the aroma, consistent aerosol delivery of the aroma, and improved capability for rapid vaporization.

It is a further object of the present invention to provide a device and method for delivering other formulations that benefit from dispersion as an aerosol. These include, for example, anti-microbial agents; insect repellants; attractants; sterilizers; confusants; pheromones; fumigants; odor neutralizers; therapeutic agents, such as menthol and eucalyptus; animal mood control agents; household cleaning products, such as surface cleaning agents, surface modification agents for aesthetic benefits, surface protection agents, and sanitization/disinfectant agents; household laundry care products, such as stain-removing agents, fabric fresheners, and other fabric treatment agents for aesthetic benefits; personal cosmetic care products for body cleaning, body lotion, and sunscreen products for humans; and consumer adhesives. Formulations, especially for aromas, are oil-based, but other carriers may be used such as water, polymers, or organic solvents.

BRIEF SUMMARY OF THE INVENTION

In one aspect, the present invention provides a method of using EHD to create a spray having a generally-consistent flowrate, preferably an aerosol spray that rapidly vaporizes; wherein capillary action wicks a liquid from a liquid source to an EHD comminution site; a first electrical potential, preferably a high-voltage potential, is applied to a location away from the liquid source and near the EHD comminution site, preferably in or near a tapered portion of a capillary element; a second electrical potential, preferably a ground, is applied to a location external to the EHD comminution site, preferably to enhance the spray without directing the spray.

In another aspect, the present invention provides a method of using EHD to create a spray, preferably an aerosol spray, wherein the spray is controllably emitted intermittently at a generally-consistent flowrate.

In another aspect, the present invention provides a method of using EHD to maintain a desired/perceived level of fragrance over an extended period of time (e.g., weeks or months).

In another aspect, the present invention provides a method of using EHD to create a spray, preferably an aerosol spray, by providing a length of capillary wick having a first and second segments contiguous at a first location, the second segment including at least one EHD comminution site; contacting the capillary wick first segment with a liquid source at a second location spaced from the first location; applying a first electrical potential to the capillary wick at the first location; positioning a reference electrode, preferably a ground, external to the capillary wick; and electrohydrodynamically producing a spray, preferably an aerosol spray, from the at least one EHD comminution site at a generally-consistent flowrate.

In yet another aspect, the present invention provides an EHD apparatus for creating a generally-consistent flowrate spray, preferably an aerosol spray, comprising a reservoir for containing a source of EHD-comminutable liquid; a capillary element, preferably a capillary wick, comprising an EHD comminution site, positioned to contact the liquid source; a first charge source, preferably a high-voltage electrode, positioned in a spaced-apart relation to the liquid source and operably proximate the EHD comminution site; and a second charge source, preferably a ground, positioned external to the EHD comminution site.

In yet another aspect, the present invention provides an EHD apparatus for creating a generally-consistent flowrate spray, preferably an aerosol spray, comprising a first charge source, preferably a high-voltage electrode, positioned in contact with the capillary element.

In yet another aspect, the present invention provides an EHD apparatus for creating two or more generally-consistent flowrate sprays, preferably aerosol sprays, comprising two or more optionally curvilinear capillary wicks in liquid contact with two or more sources of EHD-comminutable liquid.

In yet another aspect, the present invention provides an EHD apparatus for creating a generally-consistent flowrate spray, preferably an aerosol spray, comprising a housing formed to include an aperture, the aperture formed to include a charge source; a source of EHD-comminutable liquid; a capillary wick, comprising an EHD comminution site, the capillary wick at least partially within the aperture, the EHD site external to the housing, and the capillary wick in liquid communication with the liquid source; and a ground operably proximate the EHD comminution site.

BRIEF DESCRIPTION OF THE SEVERAL VIEWS OF THE DRAWINGS

The following detailed description of the embodiments of the invention will be more readily understood when taken in conjunction with the following drawings, wherein.

DETAILED DESCRIPTION OF THE INVENTION

Figure 1:
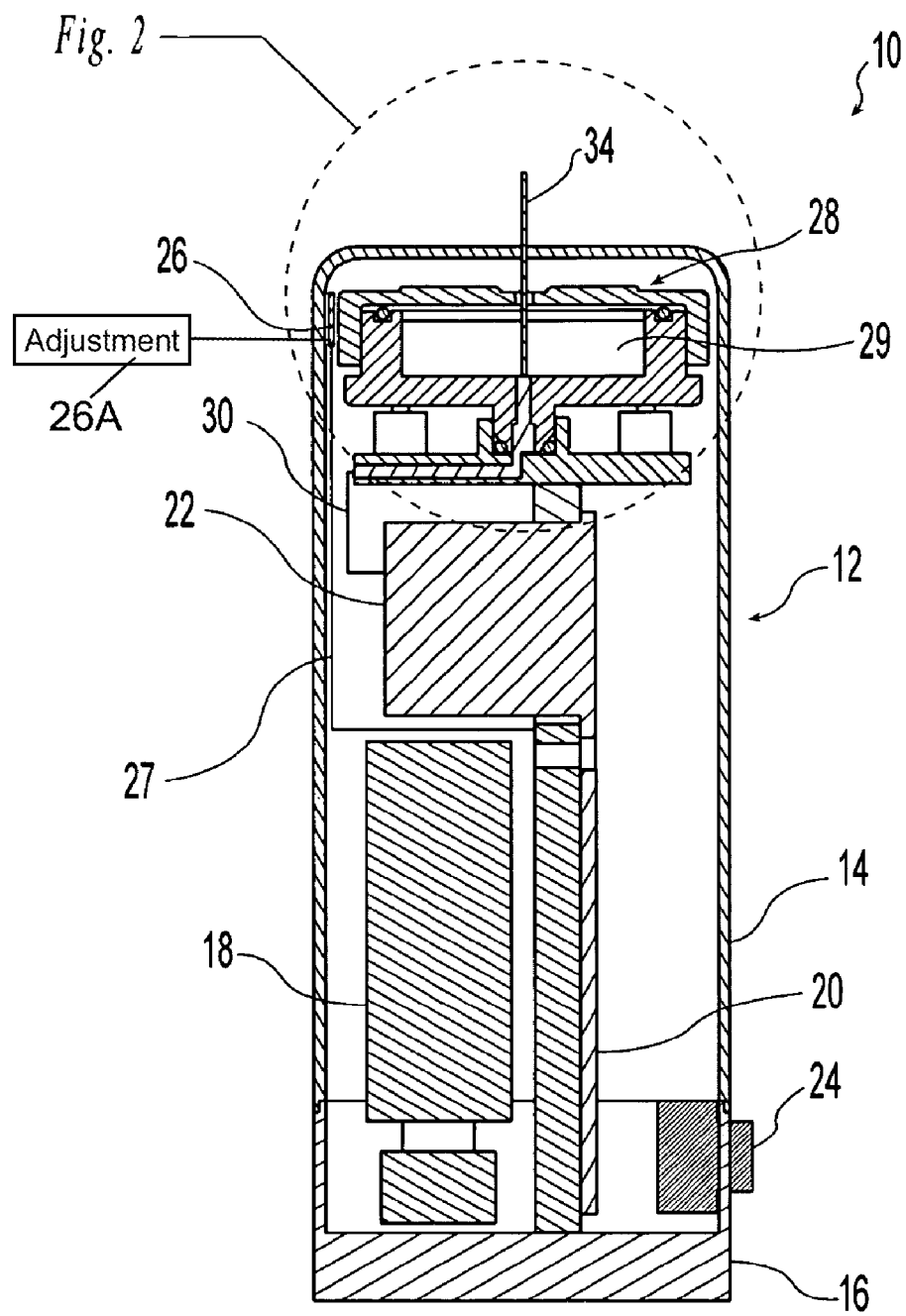
FIG. 1 is a schematic cutaway of an embodiment of the present invention and illustrating its components.
Figure 2:
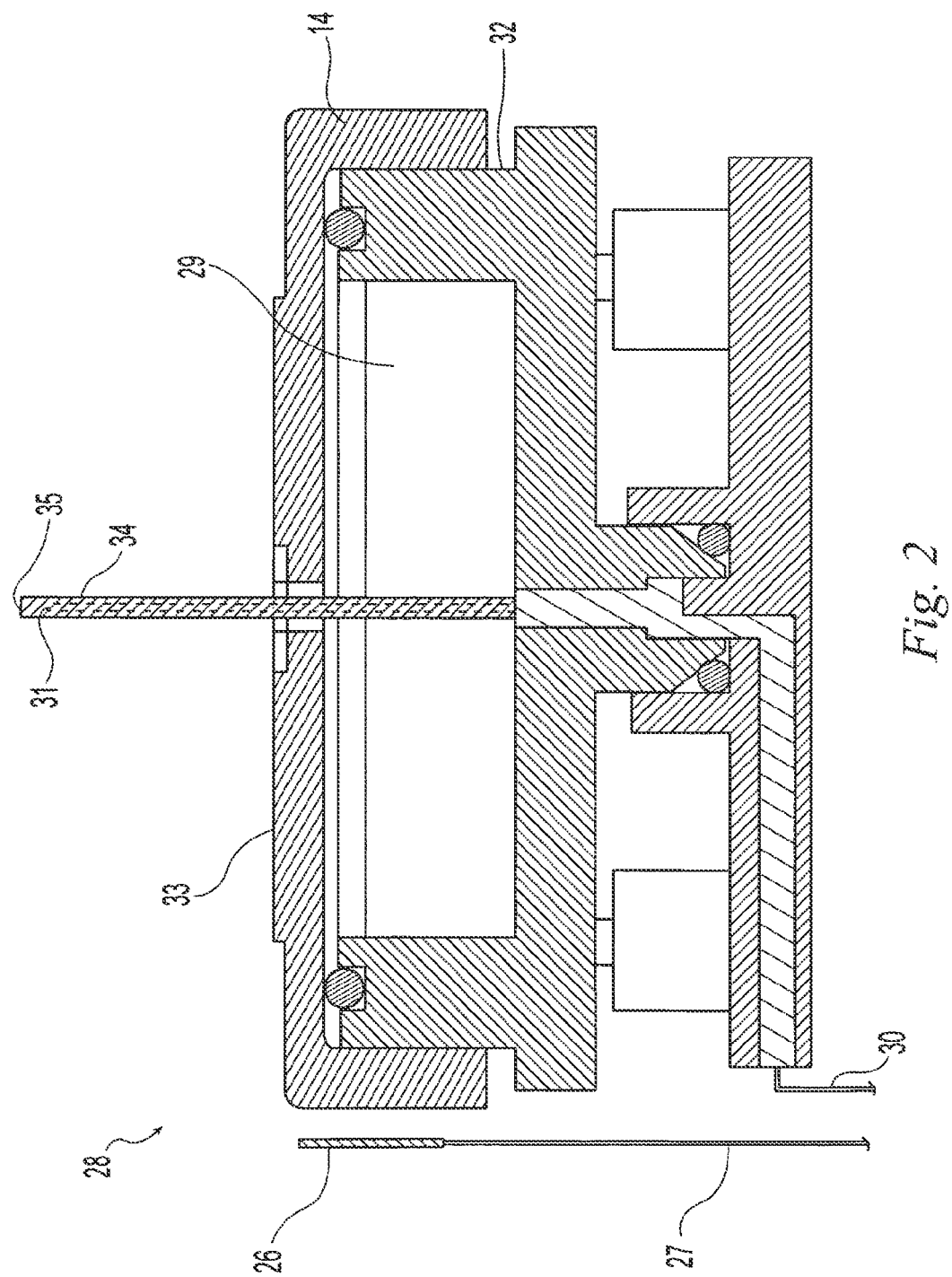
FIG. 2 is a partial detailed schematic cutaway of the embodiment of the present invention shown in FIG. 1.

EHD comminution entails the use of high voltages to charge liquids so that the electric charge on the liquid overcomes the surface tension of the liquid and the liquid is broken up, or comminuted, into a spray of fine aerosol droplets. In doing so, droplet size and droplet size distribution may be closely controlled. Droplet size may be in the sub-micron range, thus enabling rapid vaporization of the aromatics without denaturing and effecting a rapid onset of a perceived fragrance. Turning to FIGS. 1 and 2, to induce this action, the liquid must experience a high electric field, but preferably only at the point of comminution, known as the spray site, or EHD comminution site 35. To accomplish this, the bulk liquid 29 in the reservoir 32 may be charged and the charge is conducted through the liquid to the EHD comminution site 35 at the tip of the delivery column 34. To create the required electric field, an opposing electrode, often referred to as a reference or inducing electrode, and often a ground 26, is spaced away from the spray site 35 to help generate a well-defined field. In applications where the liquid exhibits relatively high resistivity, such as with many aroma oils, or is semi-conductive, it is possible to induce a potential differential across the liquid itself if sufficiently high voltage is applied between the reservoir 32 and the reference electrode 26 and electric current flows through the highly-resistive liquid. As this happens, however, undesirably high levels of electric field pumping may occur.

There are, in fact, two liquid movement mechanisms at play. The first is the capillary action associated with the liquid interaction (liquid surface tension, dynes/cm) with the surface energy of the capillary means (dynes/cm). The second is the electric field pumping due to the high voltage imposed on the liquid to induce aerosolization. It has been found that when a high-voltage charge sufficient to induce EHD spraying is applied to the bulk liquid, even near the capillary inlet for aroma and aerosol generation, a high degree of liquid delivery variability results at the EHD spray site at the opposite end of the capillary. It is believed that high-voltage pumping may contribute to the mechanism of liquid movement in the capillary at voltages necessary for EHD spraying, and that the voltage gradient along the capillary results in inconsistent movement through the capillary voids, particularly when fluid levels in a supply reservoir change over time.

Turning again to FIGS. 1 and 2, an embodiment of the present invention is shown. The dispensing device 10 generally comprises a housing 12; a liquid source 29, preferably contained within a reservoir 32; a voltage source, generally an electrode 31; a capillary element 34 terminating in an EHD comminution site 35, generally, a capillary element with an associated electrode 31; and a reference electrode, or ground 26, 27. Additionally, the dispensing device 10 may comprise a removable cap 14 that allows access to the internal components of the device 10, a base 16 to further contain the internal components and to provide a stable platform for the device 10 when placed upon a horizontal surface, a battery 18, a high-voltage power supply 22 to convert voltage (e.g., 9V) from the battery 18 to the higher, kV-level voltage required for operation of the device 10, a circuit board 20 to handle the electronics functions such as timing, voltage control, operational indicators (e.g., lights, and control of intensity and delivery rate), a high-voltage lead 30 running between the output of the high-voltage power supply 22 and the electrode 31, and a switch 24 to control operation of the device 10. The optional light (not shown) may optionally contribute to a burning candle-like appearance for the device 10 or may be used to illuminate the spray, evoking a fountain-like effect. Optionally, the device may also comprise various control features to allow a user to adjust the spray and timing of the device.

In operation, liquid is supplied to the delivery column 34, 64 (e.g., FIG. 3c) from the liquid source 29. The delivery column 34, 64 generally comprises a capillary element 46, 66 (FIG. 3) which may be formed from a capillary tube 46 (FIG. 3a) or a wick 66 (FIG. 3c) which will enable the liquid to be drawn toward the EHD comminution site tip 35 where a voltage charge causes the liquid to EHD comminute into an aerosol. As described above, placement of the electrode 31, 68 is important to providing consistent liquid and aerosol delivery rates. Capillary action has been shown to be an effective method for moving liquid from the reservoir 32 to the EHD comminution site 35. However, there may be inconsistencies in delivery rate of the liquid to the site 35 and of the aerosol to the surrounding air, possibly caused by electric field pumping, the result of the high voltage imposed on the liquid to induce aerosolization causing electric current flow through the liquid. This high voltage over the entire length of the delivery column 34, 64, however, is believed to cause electric field pumping to contribute to and result in inconsistent liquid flow rates. By minimizing this electric potential differential over the liquid path, consistent liquid delivery rates may be achieved. Advantageously, by using the capillary element 46, 66 to move liquid from the liquid source 29 to the EHD comminution site 35, active pumping of any kind, including positive-displacement, is avoided. Importantly, too, the flowrate of the spray can remain generally-consistent over the delivery of the liquid in the reservoir 32.

Many capillary elements are possible. The important attribute is the ability to deliver the liquid from the liquid source 29 to the EHD comminution site 35. The rate of capillary delivery must be sufficient to at least match the rate of EHD comminution or the EHD comminution site 35 will be starved of liquid and aerosolization will cease, or at a minimum aerosolization oscillates as liquid partially replenishes the EHD comminution site 35 and is sprayed away. Capillary tubes 46 (FIG. 3a), capillary tubes 46 filled with a porous material 56 (FIG. 3b), and fiber-like wicks 66 (FIGS. 3c-3h) have been used successfully. A sample of common off-the-shelf paper towel material formed into a capillary element has been used successfully.

Tubing materials include ABS, rigid PVC, polyester, polyamide, glass, Teflon® (poly-tetrafluoroethylene), PEEK, and polyimide. To maximize the capillary action using polymer tubes, an acceptable adhesion to the tube occurs when the surface energy of the polymer is greater than the surface tension of the liquid, preferably about 8-10 dynes/cm or more greater than the surface tension of the liquid. In spraying aromatic oils with surface tensions in the range of 27-30 dynes/cm, for example, preferred materials would include (with representative surface energy values) ABS (35-42 dynes/cm), rigid PVC (39 dynes/cm), polyester (41-44 dynes/cm), polyamide (ca. 36 dynes/cm), and polycarbonate (46 dynes/cm). While preferred, the capillary tube 46 need not be a single element. Multiple tubes and multiple tubes clustered together may be used. The capillary tube 46 need not be limited to a cylinder with a single opening. For example, two or more tubes may be coaxially combined to create a central aperture along with one or more annular apertures.

In accordance with the present invention, open-cell, porous, or fiber-like wicks are most preferred for spraying aromatic aerosols. By way of example only, and not limitation, wicks include plotter pen wicks, felt nibs, china bristles, twisted nylon twine, braided shoelaces, foam materials, and candle wicks. Materials may be polymeric, such as polyester, or natural, such as cotton. Exemplary, the porous wicking material has an open cell structure with a porosity of about 40 percent. Preferably, the voids have consistent size and shape and the wicks exhibit uniformity from one wick to another. Preferably, each wick has a well-defined tapered, conical tip that is consistent from wick to wick. Preferably, each conical tip has a low height-to-diameter aspect ratio, but high enough to provide an effective EHD comminution site 35.

Figure 4:
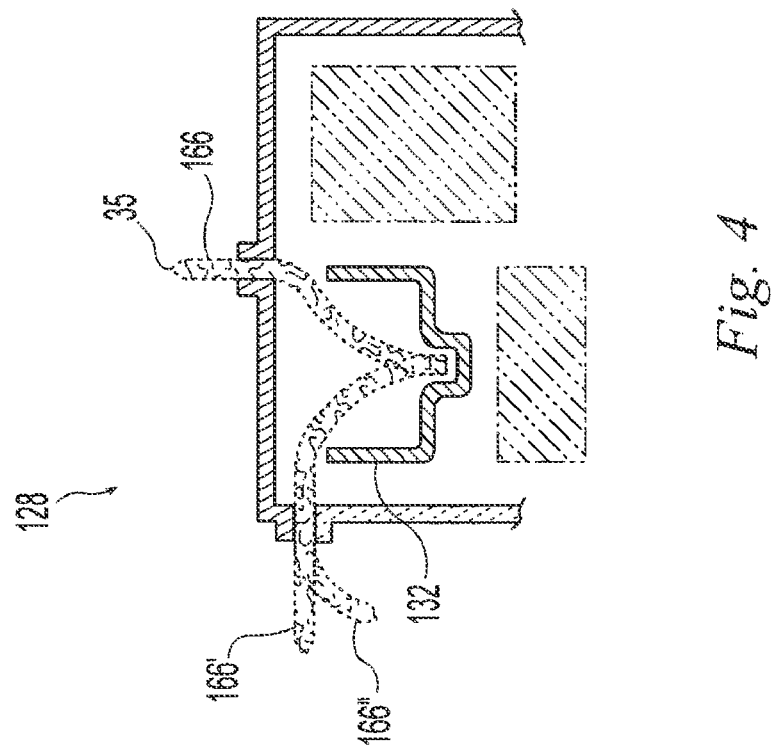
FIG. 4 is a schematic cutaway of an embodiment of the present invention illustrating optional curvilinear capillary elements and an optional offset reservoir.

Further, the present invention enables flexibility in design. Multiple capillary elements or wicks (FIG. 4) may be configured with multiple reservoirs (not shown) within the same dispensing device. As shown in FIG. 4, the capillary elements 166 may have curvilinear shapes to allow for placement of the spray sites, and positioning of the reservoir(s) 132 and other internal operational elements as required for a particular application. The size and shape of the other elements or desired placement of replaceable reservoirs may dictate non-symmetrical apparatus designs, irregularly-shaped reservoirs 132, and curvilinear capillary elements 166. There may be multiple spray sites drawing from a single reservoir. Where there are multiple reservoirs (not shown), multiple liquids may be sprayed either simultaneously or in a timed sequence. This latter capability enables the ability to dispense a first aroma and then cycle through separate aromas, thereby providing a continuous level of perceived fragrances and avoiding the phenomenon of olfactory saturation.

A key element in the present invention is the placement of the electrode 48, 68 relative to the capillary element 46, 66, specifically relative to the EHD comminution site 35. As discussed above, if the electrode 48, 68 is placed in the bulk liquid in the reservoir 32, even if placed near the bulk liquid end of the capillary element 46, 66 in the liquid, high voltages are required to effect aerosolization at the EHD comminution site 35, especially with liquids having high resistivities, with resultant high levels of electric field pumping which produce inconsistent delivery rates.

Viewing the capillary element 46, 66 as a column of liquid, it acts as a resistive element to the electric potential between the electrode 68' (FIG. 3c) and the EHD comminution site 35 at the end of the capillary element 46, 66. A longer path effects a higher resistance and voltage drop which leads to the need for a higher electric potential and a less-consistent flowrate of aerosol. By reducing the distance between the EHD comminution site 35 and the electrode 68, the resistance and voltage drop decrease, the required voltage decreases, and a more-consistent flowrate of aerosol results. Thus, the present invention limits electric field pumping to a smaller length of the capillary element 46, 66. However, as shown in FIG. 3, the electrode 48, 68, 78, 88, 88', 98, 98', 108 does not extend beyond the EHD comminution site 35; some material of the capillary element covers or extends beyond the electrode. This is where the liquid gathers via capillary action to be available to the high-voltage charge to aerosolize it. As a result, the present invention improves delivery rates, allowing for consistent, repeatable delivery rates over time. In the field of aroma delivery, for example, this may be very desirable.

The main factors in placing the electrode 68 to reduce or eliminate electric field pumping is proximity to the spray tip 35 and sharpness of the tip 35. Minor factors include liquid resistivity, capillary uptake, aerosolization rate, and position of the ground 26. In practice, the electrode 68 must be placed operably, or effectively, proximate the EHD comminution site 35. That is, the position of the electrode 68 relative to the EHD comminution site 35 must be adjusted to produce a consistent aerosol delivery rate given the properties noted above. Not only may consistent delivery rates be achieved during each "on" cycle (discussed below), consistent delivery rates may be achieved over extended periods of "on" and "off" cycles.

As a measure of consistency over a series of tests, the percent $C_V$ was calculated by dividing the standard deviation by the mean. This measurement allows for comparing equally various wicks and configurations. The lower the $C_V$, the more consistent the flowrate. By changing the charge location, for example from 68' to 68, the percent $C_V$ improved (was reduced) in the range of three to 15 percentage points. For example, one wick improved from 28.7 percent $C_V$ to 19.3 percent $C_V$. For aromas, the preferred percent $C_V$ is less than 20, more preferably less than ten. Much below ten percent is barely discernable by the average human olfactory senses. In general, the position of the charge electrode 68 has been found to be within the conical portion of the spray tip. As an example, for non-conducting wicks tested, the position of the charge source 68 has been in the range of 0.020 inches to 0.250 inches from the comminution site 35 to the charge point 68. The measurement for a conducting wick would be virtually zero.

Figure 3D:
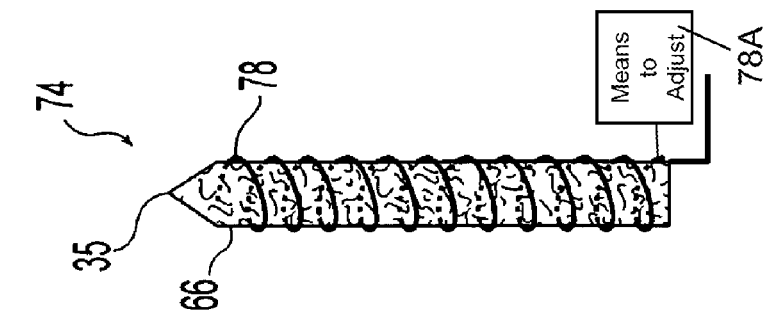
FIGS. 3a-3h are schematic cutaways of various capillary means with associated electrodes according to further embodiments of the present invention.
Figure 3C:
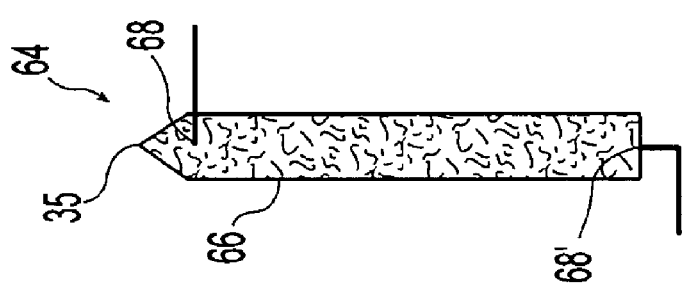
Figure 3B:
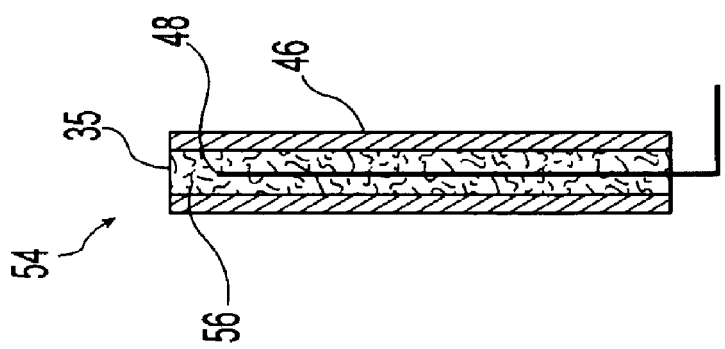
Figure 3A:
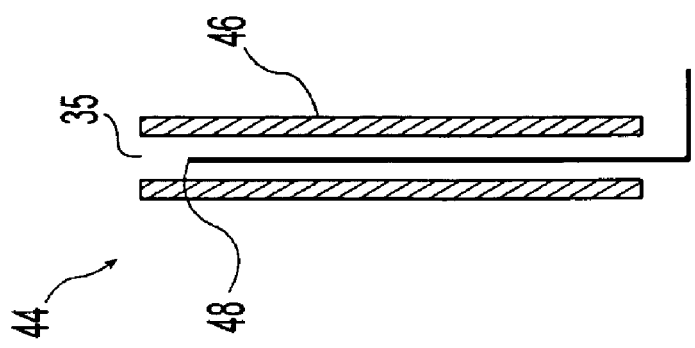
Figure 3H:
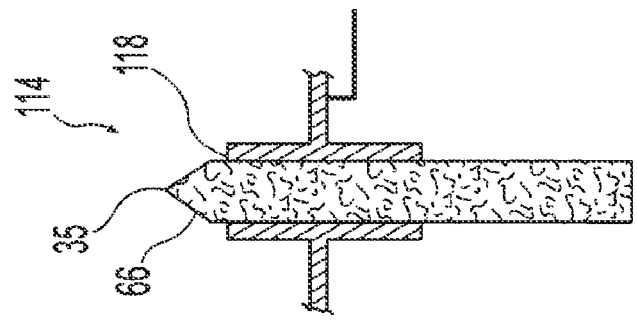
Figure 3G:
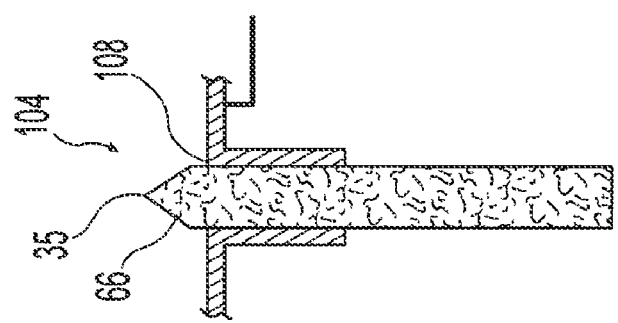
Figure 3F:
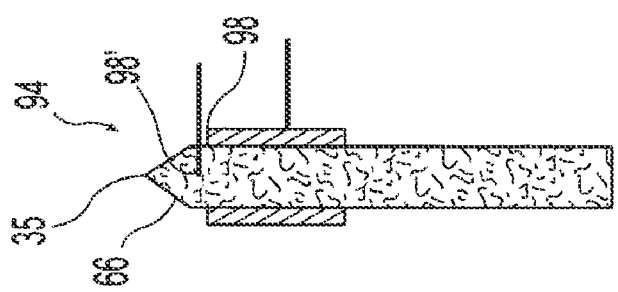
Figure 3E:
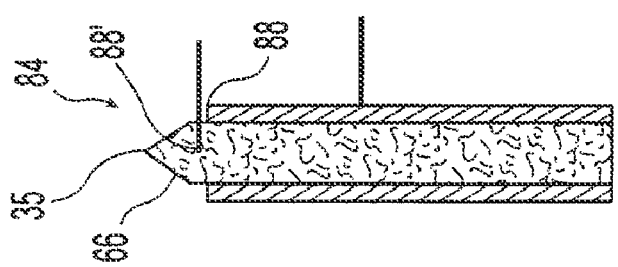
Figure 5:
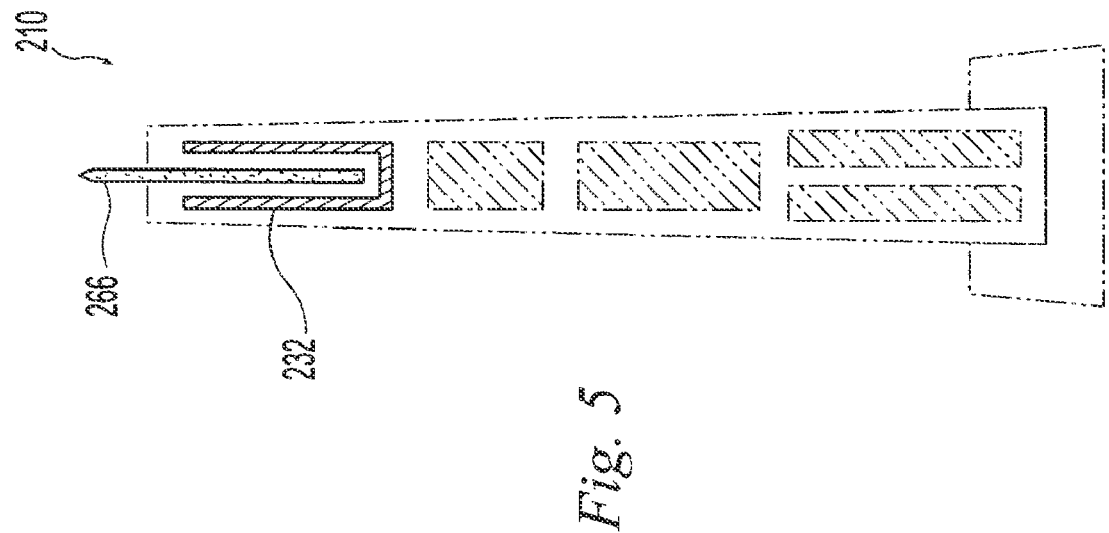
FIG. 5 is a schematic cutaway of an embodiment of the present invention illustrating a spray device comprising a taper-like candle configuration and showing a narrow and deep liquid reservoir.

Numerous electrode embodiments are feasible, all producing the same desired result of improved consistency of aerosol delivery rates with reduced electric field pumping. Importantly, as discussed above, the electrode 68 is placed away from the bulk liquid and the liquid uptake and nearer the EHD comminution site 35 to reduce the large voltage differential between the electrode 68 and the EHD comminution site 35. Illustrated in FIG. 3 are various possible electrode configurations relative to the capillary element 64 and the EHD comminution site 35. FIG. 3a shows a basic capillary element 44 comprising a capillary tube 46 with a voltage source electrode 48 positioned within the tube 46. As liquid is drawn into the tube 46, the electrode 48 provides a charge at the EHD comminution site 35 sufficient to aerosolize the liquid. The effects of electric field pumping are limited to that portion of the tube 46 between the voltage source electrode 48 and the EHD comminution site 35. FIG. 3b shows a similar arrangement, but with a porous material 56 disposed within the capillary tube 46. Operation of the capillary element 54 shown in FIG. 3b is similar to that of the capillary element 44 shown in FIG. 3a. As shown in FIG. 3c, a capillary element 64 may comprise a porous wick 66 into which is inserted a voltage source electrode 68. The embodiment shown in FIG. 3c provides a voltage source 68 inserted into the wick 66 near the EHD comminution site 35. As in the previous embodiments, the electric field pumping is controlled and consistent aerosol delivery results. With just the voltage source electrode 68 operative, it is possible, in some embodiments, to have small amounts of undesirable electric field pumping downward and counter to the upward capillary action flow. This may be countered by positioning an additional voltage source electrode 68' as shown. Thus, the electrical potential across the wick 66 may be equalized, or nearly so, and there is little or no counter electric field pumping. Turning now to FIG. 3d, yet another embodiment of a capillary element 74 is shown. Here, a voltage source electrode 78 comprises a helical coil positioned coaxial with the porous wick 66. As long as the voltage source electrode 78 is positioned operably proximate the porous' wick 66, whereby a sufficient charge is imposed on the liquid, electric field pumping is controlled, and consistent aerosol delivery results. Means 78A may be provided for enabling a user to adjust the position of a first charge source, such as electrode 78, see FIG. 3d. Counter electric field pumping is also minimized or eliminated. FIGS. 3e-3h illustrate yet other embodiments of the capillary element 84, 94, 104, 114 of the present invention. The voltage source electrode 88, 98, 108, 118 may comprise a sheath surrounding the porous wick 66 as shown or, alternatively, the voltage source electrode may comprise arcuate tabs or the like (not shown) which may be positioned operably proximate the porous wick. Finally, FIGS. 3g and 3h illustrate an embodiment wherein a portion of the housing 12 or reservoir cover 33 is formed to include the voltage source electrode 108, 118. Plastic materials of construction (with their respective nominal ohm/square resistivities) for such voltage source electrodes 108, 118 include anti-static (E9-E12), static dissipative (E6-E9), and conductive plastics (E3-E6).

To improve aerosol delivery, maximize aroma dispersion, and improve plume intensity and shape, it is preferred to place a ground or other reference electrode 26 operably proximate the EHD comminution site 35. FIGS. 1 and 2 show an example of the placement of the ground 26. If the ground 26 is placed too far from the EHD comminution site 35, the charge at the site 35 does not "see" the ground 25 and its effects are not noticeable. If the ground 26 is placed too close to the EHD comminution site 35, the aerosol spray may be misdirected toward the ground 26. Preferably, the ground 26 is placed to generate an electric field required to produce an aerosol without causing the spray to be attracted to the ground 26. The optimal position of the ground 26 will depend upon the particular configuration of the device 10. The liquid properties, particle size, spray site geometry, and corresponding electric field potential needed may affect the placement of the ground 26. Referring to FIG. 1, the ground 26 is positioned off to the side and near the top of the delivery module 28 or just below the capillary element 34. The ground 26 may be a neutral or opposite charge to the aerosol particles spraying from the EHD comminution site. Alternatively, depending upon the application, the electrode 26 may be disposed closer to the site 35 to purposely direct the aerosol spray. If desired, the ground 26 may comprise an adjustment 26A to allow varying of the position of the ground 26. The materials used for the ground 26 may be any conductor, including, but not limited to, metals and plastics. The aerosol produced is preferably charged, but may be discharged and dispersed as neutral particles for selected applications. Alternatively, an external ground reference electrode 26 may be utilized. For example, an object or an animal, human or otherwise, may provide the ground reference.

Preferably, various timing and control mechanisms are included as elements on the circuit board 20 or elsewhere. When the device 10 is initially activated in a room to emit an aroma(s), for example, it may be desirable to introduce a quantity of aroma sufficient to provide scent to the entire room after which the device 10 would shut off. Later, it may be desirable to periodically introduce a "maintenance" amount of scent to keep the level in the room constant and to counter the tendency of aromas to deaden or desensitize the sense of smell over time. This could be done by timing short sprays of perhaps several seconds duration with longer periods of quiescence. Such timing could also be used with multiple sprays having the same or different formulations. Depending upon the strength of the aroma, longer "on" times, upwards of one minute or more, may produce "hot spots" where the fragrance may become overwhelming. In these situations, the "off" time may be a minute or more.

Having multiple fragrances in a single dispenser 10 enables several other types of operation. For example, fragrances that are related to each other may collectively produce a "bouquet" effect. By controlling dispensing to specific times of the day, one fragrance may induce an invigorating effect (morning), a calming, or stress-relieving effect (mid-day), and yet another, a relaxing effect (evening).

Using a timing mechanism the device 10 may maintain a constant delivery rate even if fluid flow rate declines over time. For example, the delivery rate may be maintained through shorter spray intervals within a spray cycle time. Thus, if less liquid flows through the capillary wick 66 over time, a spray "on" interval may increase from, for example, five seconds to greater than five seconds. Alternatively, or in combination, the "off" time interval may decrease from, for example, 45 seconds to less than 45 seconds. These timing schemes can create an effective or perceived level of constant aroma delivery to the air.

Many aromatic formulations have resistivities of greater than 5 E3 ohm-cm and surface tensions of between ten to about 50 dynes/cm. To produce an aerosol from these formulations, typical voltage levels are 3-10 kV and higher. For cost and battery-life considerations, it is preferred to maintain the required voltage to a minimum. Flowrates may be 0.005-0.100 μL/sec and delivery rates 5-50 mg/hr.

While the invention has been described in connection with specific embodiments for the purposes of illustration and description, it is not intended to be exhaustive or to limit the invention to the precise form disclosed. Numerous modifications and variations are possible in light of the above teaching. It is intended that the scope of the invention be limited not by this detailed description, but rather by the claims appended hereto.

We claim:

1. An apparatus, comprising:

a reservoir;

a capillary wick positioned to contact a liquid source contained within the reservoir, the capillary wick comprising an electrohydrodynamic (EHD) comminution site;

a first charge source forming a helix surrounding said capillary wick and positioned proximate the EHD comminution site; and a second charge source positioned external to the EHD comminution site, whereby upon activating the first charge source at least a portion of the liquid EHD comminutes to form a spray having a generally-consistent flowrate.

2. The apparatus of claim 1, wherein:

the capillary wick further comprises a substantially non-conducting portion.

3. The apparatus of claim 1, wherein:

the capillary wick is substantially non-conducting.

4. The apparatus of claim 1, wherein:

the capillary wick EHD comminution site is substantially non-conducting.

5. The apparatus of claim 1, wherein:

the first charge source portion is within 0.250 inches of the EHD comminution site.

* * * * *